United States Patent [19]
Vadnay et al.

[11] 4,184,360
[45] Jan. 22, 1980

[54] FILTER HOLDER FOR CIGARETTE RESEARCH TESTING

[75] Inventors: Attila Vadnay; Charles E. von Reis, both of Ann Arbor, Mich.

[73] Assignee: Gelman Sciences, Inc., Ann Arbor, Mich.

[21] Appl. No.: 920,959

[22] Filed: Jun. 30, 1978

[51] Int. Cl.² ............... A24F 47/00; G01N 1/24
[52] U.S. Cl. ............................... 73/28; 131/171 R
[58] Field of Search ............. 73/28, 23; 131/170 R, 131/171 R

[56] References Cited

U.S. PATENT DOCUMENTS

| | | | |
|---|---|---|---|
| 2,827,905 | 3/1958 | Geoffrion | 131/171 X |
| 3,224,434 | 12/1965 | Molomut et al. | 73/28 |
| 3,460,374 | 8/1969 | Parks | 131/171 R X |
| 3,686,835 | 8/1972 | Strange et al. | 73/28 X |
| 3,693,410 | 9/1972 | Robrecht et al. | 73/28 |
| 3,748,905 | 7/1973 | Fletcher et al. | 73/28 X |

*Primary Examiner*—Daniel M. Yasich
*Attorney, Agent, or Firm*—Barnes, Kisselle, Raisch & Choate

[57] ABSTRACT

A disposable testing chamber for cigarettes which includes a thin, sheet-like transparent housing element for retaining a filter disc with a conical closure element having a press-fit into the housing to seal the disc and become self-retaining in the housing, each element having a peripheral, annular wall portion in a plane normal to the axis of the chamber to register with and lie adjacent to the periphery of the filter disc.

2 Claims, 2 Drawing Figures

FILTER HOLDER FOR CIGARETTE RESEARCH TESTING

FIELD OF INVENTION

This invention relates to the field of cigarette testing in connection with tar and nicotine content of various tobaccos and the effectiveness of various filters which are built in to cigarettes.

BACKGROUND

Cigarettes are tested by placing them in a holder and subjecting the oral end to a sub-ambient pressure after lighting of the free end. The smoke resulting from this so-called "machine smoke" is passed through a disc-shaped filter which is subsequently weighed and analyzed. Previous holding devices for the cigarettes and the disc filters have comprised two connical, individually machined plastic parts which telescope together, the inner part having an outer circumferential groove to receive an O-ring seal which is pressed into the outer part to seal the chamber in which the filter disc is retained between the parties. These machined parts are relatively heavy with respect to the filter disc and are made for long range use. They have a tendency to absorb the products of combustion and thus become discolored. In addition, the weight may change with use and the change in weight together with the discrepancy in relative weight between the filter and the holder has a tendency to reduce the accuracy of the test results.

PRESENT INVENTION

The present invention contemplates an extremely light, transparent filter holder which is self-sealing and which can be weighed with the filter in place after a smoking test. The device is sufficiently inexpensive that it can be disposable after each test and thus cleaning can be avoided. The elements can be simply made in a vacuum forming process of sheet material and are so shaped that a peripheral seal is accomplished in assembly, the parts being self-retaining in assembly.

REFERRING TO THE DRAWINGS

Figure 1:
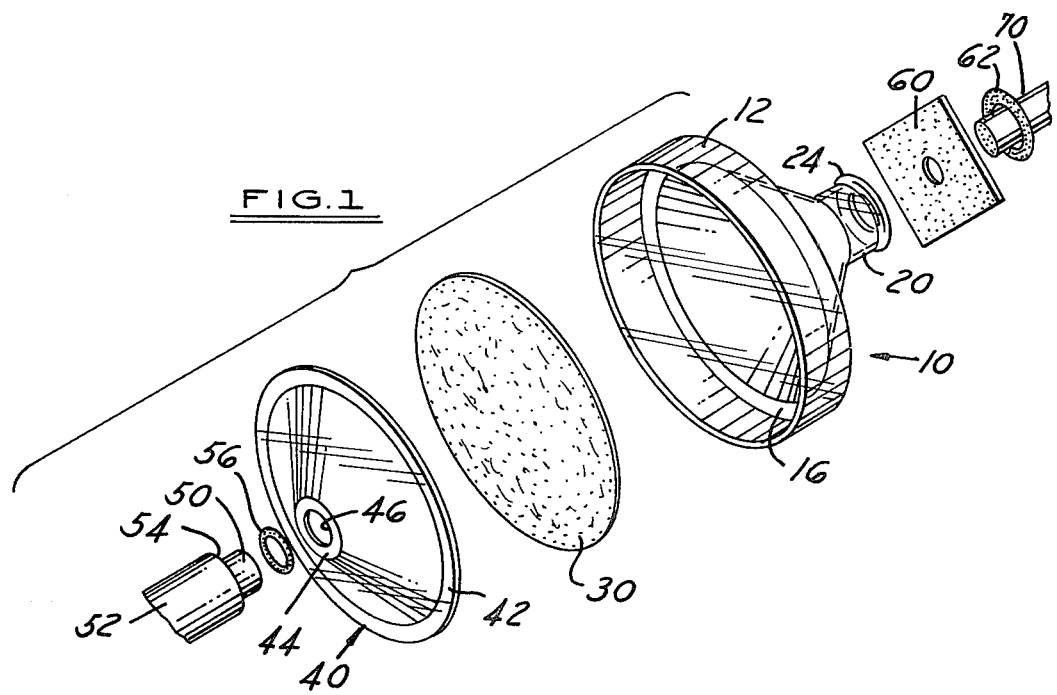
FIG. 1, an exploded view of the elements of the device showing the relationship.

The filter holder is composed of a main body portion 10 which has a cylindrical wall 12 preferably with a slight flare 14 at an open end. At the other end of the cylindrical wall is a closed end which is formed of a peripheral portion 16 which lies in a plane normal to the axis of the device, this peripheral portion extending outwardly into a conical portion 18 angling away from the body portion and terminating in a neck or nipple portion 20 which has a short inturned flange 22 around an opening which is larger than the average cigarette diameter. At the end of the nipple 20 is an annular rounded ridge 24.

The cylindrical portion 12 may have a slight taper from the back wall to the large opening for purposes which will be explained. The body portion 10 is preferably formed utilizing a vacuum forming technique so that a relatively thin sheet of transparent plastic can be shaped as indicated. A disc of sealing material is indicated in FIG. 1 at 30, this being formed of a glass fiber material in common use in this type of testing. The closure member for the device is a truncated cone 40 having a flange portion 42 at the periphery lying in a plane normal to the axis of the assembly, the conical portion terminating in a radially extending flange 44 which has an opening 46 to receive a reduced end portion 50 of a suction tube 52. A shoulder 54 extends radially to serve as a seal for an O-ring 56.

Figure 2:
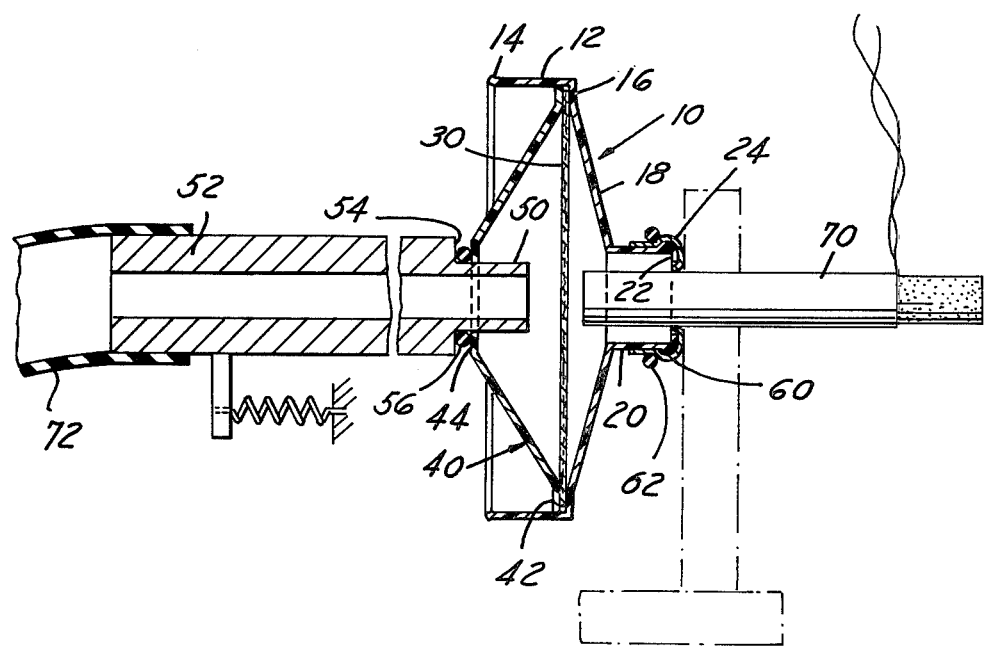
FIG. 2, an assembly view partially in section of the apparatus in operating condition.

In assembly as shown in FIG. 2, the two radially extending peripheral portions 16 and 42 of parts 10 and 40 clamp the periphery of the filter disc 30. This disc preferably has a diameter which provides a relatively loose fit within the cylindrical body portion 12 so that it may be readily inserted and removed without damage to the filter. The outer diameter will always be greater than the inner diameter of the radially extending peripheral portions 16 and 42 so that the radial extent of the annular portions 16 and 42 is sufficient to cover the periphery of the disc even though there is clearance around the edges thereof. The outer edge of the element 40 has a dimension which provides a light frictional fit with the walls of the cylinder 12 so that when the parts are assembled as shown in FIG. 2, they will be self-retaining.

The testing apparatus in which the described filter holder is used consists of a base plate (not shown) which supports a fixture at one end to receive the assembled filter and retain it on a horizontal axis. In line with the fixture is the tube 52 mounted to move horizontally in a limited motion against resilient bias which urges it toward the fixture.

The first step in the use is to install a thin perforate rubber membrane 60 over the cigarette opening and retain it with a soft rubber band 62. The assembly is then placed in the supporting fixture while the tube 52 is retracted and the end 50 of the tube is then inserted into the opening 46 of cone 40. Release of the tube causes the resilient bias to move the O-ring 56 to a sealing position against the flange 44 and also places a pressure on cone 40, moving it snugly into the main body housing 10 and putting a clamping pressure on the rim of the filter sheet 30. A cigarette 70 is then pushed through the opening in the membrane 60 where it will be sealed at the periphery of the opening and supported for test purposes. A suitable steady or pulsing suction is applied from a sub-ambient pressure source to tube 52 through a flexible conduit 72 and the cigarette is lighted at the free end in the normal manner.

The cigarette is preferably positioned endwise in the membrane 60 so that the smoke will spread over the entire disc to distribute the residuals from the smoke as it passes through the disc. Once the cigarette is consummed to the point desired, the device can be removed and weighed to determine the amount of residuals retained on the filter. If desired, the filter can be removed for analysis of these residuals. The lightness of the device as made from the thin plastic renders it particularly acceptable to research testing since the weight, which may range from 2.8 to 3 grams, makes it possible to weigh the filter with the assembly without handling and removal.

We claim:

1. A disposable filter holder for tar and nicotine testing of cigarettes which comprises:
   (a) a main body formed of relatively thin sheet plastic material having a wide, cylindrical portion open at one end and a closure wall at the other end having a tapered wall angling away from the cylindrical portion and means terminating in a relatively small opening for retaining a test cigarette, said main body being adapted to receive a filter disc, and (b) a closure cone formed of thin sheet plastic material having a central opening for a biased connection of a suction conduit to a sub-ambient pressure source and terminating in a thin peripheral edge having an outer diameter to be received in a friction fit with said cylindrical portion of said main body and to seat against said closure wall of said main body, said parts being dimensioned to fit in self-retaining position and to retain and seal a disc filter in said body between the peripheral portions of the closure wall and the closure cone without additional sealing elements when axial pressure is applied to said assembled parts by said conduit.

2. A disposable filter holder for tar and nicotine testing of cigarettes which comprises:

(a) a main body formed of relatively thin, lightweight, transparent plastic sheet material having a substantially uniform thickness, said body comprising a wide cylindrical portion open at one end and a closure wall at the other end having a peripheral radial portion lying in a plane normal to the axis of the body and a conical portion within said radial portion extending to a central, axially-extending, nipple portion for retaining a test cigarette, said main body being adapted to receive and retain a circular filter disc, and (b) a closure cone formed of relatively thin, lightweight, transparent plastic sheet material of substantially uniform thickness terminating in a peripheral radial edge lying in a plane normal to the axis of the closure cone and having a central opening for a biased connection of a suction conduit to a sub-ambient pressure source, said peripheral edge being dimensioned to be received in the cylindrical portion of said body in a frictional, self-retaining position and to retain and seal a disc filter in said body between the radial peripheral portions of the body and the closure cone without additional sealing elements when axial pressure is applied to said assembled parts through the said nipple portion of said body and the area of said closure cone around the central opening therein by said conduit.

* * * * *